United States Patent
Faig et al.

(10) Patent No.: US 10,507,169 B1
(45) Date of Patent: Dec. 17, 2019

(54) AQUEOUS GEL MASK COMPOSITIONS AND KITS

(71) Applicant: L'OREAL, Paris (FR)

(72) Inventors: Jonathan James Faig, Sayreville, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/132,988

(22) Filed: Sep. 17, 2018

(51) Int. Cl.
| | |
|---|---|
| *A61K 8/02* | (2006.01) |
| *A61K 8/04* | (2006.01) |
| *A61K 8/73* | (2006.01) |
| *A61K 8/34* | (2006.01) |
| *A61K 8/20* | (2006.01) |

(52) U.S. Cl.
CPC ............ *A61K 8/0212* (2013.01); *A61K 8/042* (2013.01); *A61K 8/20* (2013.01); *A61K 8/345* (2013.01); *A61K 8/733* (2013.01); *A61K 2800/30* (2013.01); *A61K 2800/5922* (2013.01)

(58) Field of Classification Search
CPC ...... A61K 8/0212; A61K 8/042; A61K 8/733; A61K 8/345; A61K 8/20; A61K 2800/30; A61K 2800/5922
See application file for complete search history.

(56) References Cited

PUBLICATIONS

Dr. Dennis Gross, Hyaluronic Marine Hydrating Modeling Mask; Mintel; www.gnpd.com, published Oct. 2016.

*Primary Examiner* — Shirley V Gembeh
(74) *Attorney, Agent, or Firm* — McNees Wallace & Nurick LLC

(57) ABSTRACT

An aqueous gel mask composition is disclosed including a plurality of sodium alginates constituting, by weight, between 2.2% to 4.5% of the aqueous gel mask composition, and water, wherein the aqueous gel mask composition is reactive with an activator to form a continuous film. An aqueous gel mask kit is disclosed including the aqueous gel mask composition and an activator.

23 Claims, No Drawings

AQUEOUS GEL MASK COMPOSITIONS AND KITS

FIELD OF TECHNOLOGY

The present disclosure is directed to aqueous gel mask compositions and kits including the aqueous gel mask compositions. More specifically, the present disclosure is directed to aqueous gel mask compositions and kits including a plurality of sodium alginates constituting, by weight, between 2.2% to 4.5% of the aqueous gel mask composition, and water.

BACKGROUND

Hydrating mask compositions are known, but typically include the use of fibroin and/or various rheology modifiers and thickeners, which affect the final texture of the mask. Examples of hydrating masks include Dr. Dennis Gross Skincare Hyaluronic Marine Hydrating Modeling Mask, which is described as a gel and powder hydrating treatment designed to deliver hydration to the skin. It includes a hyaluronic cushion gel and an activating powder, and is enriched with algin. This kit requires consumers to mix the hyaluronic cushion gel and the activating powder using a bowl and spatula provided before applying the mask.

There remains a need to provide an effective, aqueous gel mask composition and kit for hydrating skin that is stable, easy to use, and efficacious.

BRIEF SUMMARY

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In an exemplary embodiment, an aqueous gel mask composition includes a plurality of sodium alginates constituting, by weight, between 2.2% to 4.5% of the aqueous gel mask composition, and water, wherein the aqueous gel mask composition is reactive with an activator to form a continuous film. A first sodium alginate of the plurality of sodium alginates includes a molecular weight greater than a second sodium alginate of the plurality of sodium alginates. Less than 3%, by weight, of the aqueous gel mask composition includes sodium alginates having a molecular weight of at least 300 kDa. The plurality of sodium alginates includes an average M/G ratio between 70:30 to 50:50, an average molecular weight between 150 kDa to 425 kDa, at least 20%, by weight, of the sodium alginates having a molecular weight of at least 250 kDa, and a weight ratio of sodium alginates having a molecular weight of 75 kDa or less to sodium alginates having a molecular weight of at least 250 kDa of less than 3:2. If the plurality of sodium alginates includes two sodium alginates each having a molecular weight of at least 250 kDa, and the two sodium alginates constitute, by weight, less than 1.25% of the aqueous gel mask composition, then the two sodium alginates include an average molecular weight of less than 375 kDa.

In another exemplary embodiment, an aqueous gel mask composition includes a plurality of sodium alginates constituting, by weight, between 2.2% to 4.5% of the aqueous gel mask composition, and water, wherein the aqueous gel mask composition is reactive with an activator to form a continuous film. The plurality of sodium alginates is selected from the group consisting of: a first sodium alginate having a molecular weight between about 375 kDa and about 425 kDa, and a M/G ratio of between about 65:35 to about 70:30; a second sodium alginate having a molecular weight between about 90 kDa and about 180 kDa, and a M/G ratio of between about 60:40 to about 70:30; a third sodium alginate having a molecular weight between about 300 kDa and about 400 kDa, and a M/G ratio of between about 45:55 to about 55:45; a fourth sodium alginate having a molecular weight between about 20 kDa and about 60 kDa, and a M/G ratio of between about 25:75 to about 35:65; and combinations thereof. The plurality of sodium alginates is a formulation, by weight, selected from the group consisting of: (a) 0-0.25% of the first sodium alginate, 1-1.5% of the second sodium alginate, and 1.75-3% of the third sodium alginate; (b) 0-0.25% of the first sodium alginate, 1-2% of the second sodium alginate, 1-1.75% of the third sodium alginate, and 0-2.5% of the fourth sodium alginate; (c) 0.25-0.75% of the first sodium alginate, 1-1.5% of the second sodium alginate, and 3% of the third sodium alginate; (d) 0.25-0.75% of the first sodium alginate, 1.5-2% of the second sodium alginate, and 1-1.25% of the third sodium alginate; (e) 0.75-1.25% of the first sodium alginate, 2.25-3% of the third sodium alginate, and 0-1.25% of the fourth sodium alginate; (f) 0.75-1.25% of the first sodium alginate, 0.5-1% of the second sodium alginate, 0-3% of the third sodium alginate, and 0-1.25% of the fourth sodium alginate; (g) 0.75-1.25% of the first sodium alginate, 1-1.5% of the second sodium alginate, 0-1.5% of the third sodium alginate, and 0-2.5% of the fourth sodium alginate; (h) 1.25-1.75% of the first sodium alginate, 0-1% of the third sodium alginate, and 0-1.25% of the fourth sodium alginate; (i) 1.25-1.75% of the first sodium alginate, 0-0.5% of the second sodium alginate, and 1% of the third sodium alginate; (j) 1.25-1.75% of the first sodium alginate and 1-1.5% of the second sodium alginate; (k) 1.75-2% of the first sodium alginate and 2-2.5% of the third sodium alginate; and (l) 1.75-2% of the first sodium alginate, 0.5% of the second sodium alginate, and 1.25-2.5% of the third sodium alginate.

In another exemplary embodiment, an aqueous gel mask kit includes an aqueous gel mask composition and an activator, wherein the aqueous gel mask composition includes a plurality of sodium alginates and water, the plurality of sodium alginates constitutes, by weight, between 2.2% to 4.5% of the aqueous gel mask composition, and the aqueous gel mask composition is reactive with an activator to form a continuous film. The plurality of sodium alginates includes an average M/G ratio between 70:30 to 50:50. The plurality of sodium alginates includes an average molecular weight between 150 kDa to 425 kDa. At least 20% of the plurality of sodium alginates includes a molecular weight of at least 250 kDa. A first sodium alginate of the plurality of sodium alginates includes a molecular weight greater than a second sodium alginate of the plurality of sodium alginates. The plurality of sodium alginates includes a weight ratio of sodium alginates having a molecular weight of 75 kDa or less to sodium alginates having a molecular weight of at least 250 kDa of less than 3:2. The aqueous gel mask composition includes, by weight, less than 3% of the plurality of sodium alginates having a molecular weight of at least 300 kDa. If the plurality of sodium alginates includes two sodium alginates each having a molecular weight of at least 250 kDa, and the two sodium alginates constitute, by weight, less than 1.25% of the aqueous gel mask composition, then the two sodium alginates include an average molecular weight of less than 375 kDa.

Other features and advantages of the present disclosure will be apparent from the following more detailed description of the preferred embodiment which illustrates, by way of example, the principles of the disclosure.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The aqueous gel mask compositions and kits, according to the present disclosure, provide stable, easy to use, and efficacious compositions for hydrating skin.

In one embodiment, an aqueous gel mask composition includes a plurality of sodium alginates constituting, by weight, between 2.2% to 4.5% of the aqueous gel mask composition, and water, wherein the aqueous gel mask composition is reactive with an activator to form a continuous film. A first sodium alginate of the plurality of sodium alginates includes a molecular weight greater than a second sodium alginate of the plurality of sodium alginates. The continuous film may be an aqueous gel mask.

In a further embodiment, less than, by weight, 3%, alternatively 2.95%, alternatively 2.9%, alternatively 2.85%, alternatively 2.8%, alternatively 2.75%, alternatively 2.7%, alternatively 2.65%, alternatively 2.6%, alternatively 2.55%, alternatively 2.5%, of the aqueous gel mask composition includes sodium alginates having a molecular weight of at least 250 kDa, alternatively 275 kDa, alternatively 300 kDa, alternatively 325 kDa, or any suitable combination, sub-combination, range, or sub-range thereof.

As used herein, a "continuous film" indicates a film having a surface which is uninterrupted along the length and breadth of the film. In one embodiment, the continuous film includes an essentially homogenous composition, alternatively a homogenous composition. As used herein, an "essentially homogenous composition" indicates a composition which does not vary by more than 1% with respect to any ingredient thereof. The continuous film may have an essentially uniform thickness, alternatively a uniform thickness. As used herein, an "essentially uniform thickness" indicates a thickness which does not vary by more than 5%.

Alginates are copolymers with blocks of (1-4)-linked β-D-mannuronate (M) and its C-5 epimer α-L-guluronate (G) residues. The content of the M blocks and G blocks may be described by the M/G ratio of the alginate. The plurality of sodium alginates may include any suitable average M/G ratios, including, but not limited to an M/G ratio between 70:30 to 50:50, alternatively between 70:30 to 60:40, alternatively between 65:35 to 55:45, alternatively between 60:40 to 50:50, or any suitable combination, sub-combination, range, or sub-range thereof by weight.

The plurality of sodium alginates may include any suitable average molecular weight, including, but not limited to, between 150 kDa to 425 kDa, alternatively between 150 kDa to 200 kDa, alternatively between 175 kDa to 225 kDa, alternatively between 200 kDa to 250 kDa, alternatively between 225 kDa to 275 kDa, alternatively between 250 kDa to 300 kDa, alternatively between 275 kDa to 325 kDa, alternatively between 300 kDa to 350 kDa, alternatively between 325 kDa to 375 kDa, alternatively between 350 kDa to 400 kDa, alternatively between 375 kDa to 425 kDa, or any suitable combination, sub-combination, range, or sub-range thereof.

In one embodiment the plurality of sodium alginates includes at least, by weight, 20%, alternatively at least 25%, alternatively at least 30%, alternatively at least 35%, alternatively at least 40%, alternatively at least 45%, alternatively at least 50% of the sodium alginates having a molecular weight of at least 250 kDa, alternatively at least 260 kDa, alternatively at least 270 kDa, alternatively at least 280 kDa, alternatively at least 290 kDa, alternatively at least 300 kDa, or any suitable combination, sub-combination, range, or sub-range thereof. The plurality of sodium alginates may include any suitable weight ratio of sodium alginates having a molecular weight of 75 kDa or less to sodium alginates having a molecular weight of at least 250 kDa, alternatively at least 260 kDa, alternatively at least 270 kDa, alternatively at least 280 kDa, alternatively at least 290 kDa, alternatively at least 300 kDa, including, but not limited to, a ratio of less than 3:2, or any suitable combination, sub-combination, range, or sub-range thereof.

In one embodiment, if the plurality of sodium alginates includes two sodium alginates each having a molecular weight of at least 250 kDa, alternatively at least 260 kDa, alternatively at least 270 kDa, alternatively at least 280 kDa, alternatively at least 290 kDa, alternatively at least 300 kDa (or any suitable combination, sub-combination, range, or sub-range thereof), and the two sodium alginates constitute, by weight, less than 1.25% of the aqueous gel mask composition, then the two sodium alginates include an average molecular weight of less than 375 kDa.

In another embodiment, an aqueous gel mask composition includes a plurality of sodium alginates constituting, by weight, between 2.2% to 4.5% of the aqueous gel mask composition, and water, wherein the aqueous gel mask composition is reactive with an activator to form a continuous film. The plurality of sodium alginates is selected from the group consisting of: a first sodium alginate having a molecular weight between about 375 kDa and about 425 kDa, and a M/G ratio of between about 65:35 to about 70:30; a second sodium alginate having a molecular weight between about 90 kDa and about 180 kDa, and a M/G ratio of between about 60:40 to about 70:30; a third sodium alginate having a molecular weight between about 300 kDa and about 400 kDa, and a M/G ratio of between about 45:55 to about 55:45; a fourth sodium alginate having a molecular weight between about 20 kDa and about 60 kDa, and a M/G ratio of between about 25:75 to about 35:65; and combinations thereof. The plurality of sodium alginates is a formulation, by weight, selected from the group consisting of:
  (a) 0-0.25% of the first sodium alginate, 1-1.5% of the second sodium alginate, and 1.75-3% of the third sodium alginate;
  (b) 0-0.25% of the first sodium alginate, 1-2% of the second sodium alginate, 1-1.75% of the third sodium alginate, and 0-2.5% of the fourth sodium alginate;
  (c) 0.25-0.75% of the first sodium alginate, 1-1.5% of the second sodium alginate, and 3% of the third sodium alginate;
  (d) 0.25-0.75% of the first sodium alginate, 1.5-2% of the second sodium alginate, and 1-1.25% of the third sodium alginate;
  (e) 0.75-1.25% of the first sodium alginate, 2.25-3% of the third sodium alginate, and 0-1.25% of the fourth sodium alginate;

(f) 0.75-1.25% of the first sodium alginate, 0.5-1% of the second sodium alginate, 0-3% of the third sodium alginate, and 0-1.25% of the fourth sodium alginate;

(g) 0.75-1.25% of the first sodium alginate, 1-1.5% of the second sodium alginate, 0-1.5% of the third sodium alginate, and 0-2.5% of the fourth sodium alginate;

(h) 1.25-1.75% of the first sodium alginate, 0-1% of the third sodium alginate, and 0-1.25% of the fourth sodium alginate;

(i) 1.25-1.75% of the first sodium alginate, 0-0.5% of the second sodium alginate, and 1% of the third sodium alginate;

(j) 1.25-1.75% of the first sodium alginate and 1-1.5% of the second sodium alginate;

(k) 1.75-2% of the first sodium alginate and 2-2.5% of the third sodium alginate; and (l) 1.75-2% of the first sodium alginate, 0.5% of the second sodium alginate, and 1.25-2.5% of the third sodium alginate.

In some embodiments, there may be one or more actives present in the aqueous gel mask composition, according to the disclosure, the additive selected from, for example, sodium hydroxide, citric acid, sodium citrate; humectants, such as, but not limited to, propanediol, hydroxyethyl urea, acetamide MEA, glycols, such as, but not limited to, glycerin, propylene glycol, butylene glycol, and pentylene glycol; alcohols; antimicrobial components such as, but not limited to, phenoxyethanol, chlorphenesin, sodium benzoate, potassium sorbate, salicylic acid, alpha acid; antioxidants, including, but not limited to, phenolic compounds, such as, but not limited to, chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenol s, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin (Scutellaria Baicalensis root extract), pine bark extract (Pinus Pinaster bark/bud extract), ellagic acid; vitamins and vitamin derivatives, such as, but not limited to, tocopherol and ascorbic acid; and combinations thereof. In one embodiment, the amount of humectant present in the aqueous gel mask composition can range from about 0 to about 12%, from about 0.5 to about 6%, from about 3 to about 9%, and from about 6 to about 12%, or any suitable combination, sub-combination, range, or sub-range thereof by weight, based on the weight of the aqueous gel mask composition.

In some embodiments, there may be one or more additional components present in the aqueous gel mask composition, according to the disclosure, such as, but not limited to, solvents such as, but not limited to, propanediol, ethanol; pigments such as, but not limited to, ultramarines, titanium dioxide, chromium oxide green, water dispersible pigments and pearls; fillers such as clays, talc, mica, silica, calcium chloride, organic thickeners with for instance, anionic, cationic, nonionic, amphoteric polymeric associative thickeners, and combinations thereof; polymers such as, but not limited to, pectin; penetrants; sequestrants; emollients, such as, but not limited to sucrose; fragrances; dispersants; film-forming agents; ceramides; opacifiers, and combinations thereof. Although the aforementioned optional components are given as an example, it will be appreciated that other optional components compatible with cosmetic applications known in the art may be used.

In one embodiment, the amount of pigments present in the aqueous gel mask composition can range from about 0 to about 2%, or any suitable combination, sub-combination, range, or sub-range thereof by weight, based on the weight of the aqueous gel mask composition.

In one embodiment, the amount of solvents present in the aqueous gel mask composition can range from about 0 to about 3%, or any suitable combination, sub-combination, range, or sub-range thereof by weight, based on the weight of the aqueous gel mask composition.

In accordance with the various embodiments, the amount of actives and additional components present in the aqueous gel mask composition can range from about 0 to about 50%, from about 0.5 to about 30%, from about 1.5 to about 20%, and from about 5 to about 15%, or any suitable combination, sub-combination, range, or sub-range thereof by weight, based on the weight of the aqueous gel mask composition. Thus, one or a combination of optional components may be present, by weight, based on the total weight of the composition, each one or the combination present from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

In one embodiment, the aqueous gel mask composition includes glycerin. Glycerin may constitute any suitable portion of the aqueous gel mask composition, including, but not limited to, between about 10% to about 20% of the aqueous gel mask composition, alternatively between about 10% to about 15%, alternatively between about 12.5% to about 17.5%, alternatively between about 15% to about 20%, alternatively between about 14% to about 16%, alternatively about 15%, or any suitable combination, sub-combination, range, or sub-range thereof.

In one embodiment, the aqueous gel mask composition includes phenoxyethanol. Phenoxyethanol may constitute any suitable portion of the aqueous gel mask composition, including, but not limited to, by weight, between about 0.05% to about 0.7% of the aqueous gel mask composition.

In one embodiment, the aqueous gel mask composition includes chlorphenesin. Chlorphenesin may constitute any suitable portion of the aqueous gel mask composition, including, but not limited to, by weight, between about 0.20% to about 0.27% of the aqueous gel mask composition.

In one embodiment, the aqueous gel mask composition includes sodium benzoate, potassium sorbate, or both. Sodium benzoate and potassium sorbate combined may constitute any suitable portion of the aqueous gel mask composition, including, but not limited to, by weight, up to about 0.1% of the aqueous gel mask composition. In another embodiment, the aqueous gel mask composition is free of sodium benzoate, potassium sorbate, or both.

The aqueous gel mask composition may further include propanediol. Suitable levels of propanediol include, but are not limited to, between about 2% to about 4% of the aqueous gel mask composition, alternatively between about 2% to about 2.5%, alternatively between about 2.25% to about 2.75%, alternatively between about 2.5% to about 3%, alternatively between about 2.75% to about 3.25%, alternatively between about 3% to about 3.5%, alternatively between about 3.25% to about 3.75%, alternatively between about 3.5% to about 4%, or any suitable combination, sub-combination, range, or sub-range thereof.

In one embodiment, the aqueous gel mask composition is free of fibroin, rheology modifiers, thickeners, lithium magnesium sodium silicate, sodium hyaluronate, *Oryza sativa* powder, xanthan gum, ethylenediaminetetraacetic acid, conchiolin powder, dehydroacetic acid, benzyl alcohol, or combinations thereof.

In one embodiment, the first sodium alginate includes a molecular weight between about 375 kDa and about 425 kDa, and a M/G ratio of between about 65:35 to about 70:30 (commercially available as Protonal PH6160).

In another embodiment, the first sodium alginate includes a molecular weight between about 300 kDa and about 400 kDa, and a M/G ratio of between about 45:55 to about 55:45 (commercially available as Protonal HF 120 RBS).

In one embodiment, the second sodium alginate includes a molecular weight between about 300 kDa and about 400 kDa, and a M/G ratio of between about 45:55 to about 55:45.

In another embodiment, the second sodium alginate includes a molecular weight between about 90 kDa and about 180 kDa, and a M/G ratio of between about 60:40 to about 70:30 (commercially available as Protonal CR 8133).

In yet another embodiment, the second sodium alginate includes a molecular weight between about 20 kDa and about 60 kDa, and a M/G ratio of between about 25:75 to about 35:65 (commercially available as Protonal LFR 5/60).

In one embodiment, the first sodium alginate and the second sodium alginate are selected from the group consisting of sodium alginate materials characterized by: a molecular weight between about 375 kDa and about 425 kDa, and a M/G ratio of between about 65:35 to about 70:30; a molecular weight between about 90 kDa and about 180 kDa, and a M/G ratio of between about 60:40 to about 70:30; a molecular weight between about 300 kDa and about 400 kDa, and a M/G ratio of between about 45:55 to about 55:45; and a molecular weight between about 20 kDa and about 60 kDa, and a M/G ratio of between about 25:75 to about 35:65.

In a further embodiment, wherein the plurality of sodium alginates further includes a third sodium alginate having a molecular weight less than the second sodium alginate and being selected from the group consisting of sodium alginate materials characterized by: a molecular weight between about 300 kDa and about 400 kDa, and a M/G ratio of between about 45:55 to about 55:45; and a molecular weight between about 20 kDa and about 60 kDa, and a M/G ratio of between about 25:75 to about 35:65.

In yet a further embodiment, the plurality of sodium alginates further includes a fourth sodium alginate, the first sodium alginate includes a molecular weight between about 375 kDa and about 425 kDa, and a M/G ratio of between about 65:35 to about 70:30, the second sodium alginate includes a molecular weight between about 90 kDa and about 180 kDa, and a M/G ratio of between about 60:40 to about 70:30, the third sodium alginate includes a molecular weight between about 300 kDa and about 400 kDa, and a M/G ratio of between about 45:55 to about 55:45, and the fourth sodium alginate includes a molecular weight between about 20 kDa and about 60 kDa, and a M/G ratio of between about 25:75 to about 35:65.

In one embodiment, the aqueous gel mask composition includes glycerin and propanediol, wherein the plurality of sodium alginates constitutes, by weight, about 3.4% of the aqueous gel mask composition, the water constitutes, by weight, between about 74% to about 78% of the aqueous gel mask composition, the glycerin constitutes, by weight, about 15% of the aqueous gel mask composition, and the propanediol constitutes, by weight, about 3% of the aqueous gel mask composition.

The aqueous gel mask composition may include any suitable amount of water, by weight, including, but not limited to, between about 70% to about 80%.

In one embodiment, an aqueous gel mask kit includes an aqueous gel mask composition and an activator.

The activator may have any suitable form, including, but not limited to, a film, a liquid, and combination thereof. The activator may be applied by overlaying a film, by spraying a liquid, by misting a liquid, by painting a liquid, or combinations thereof. In one embodiment, the activator is a liquid and is disposed in a spraying or misting apparatus. The activator may include any suitable amount of the divalent cation, such as calcium, copper, zinc, and manganese), including but not limited to, by weight, about 0.1% to about 3%. In one embodiment, the activator is water soluble. In a further embodiment, the activator is soluble in an aqueous formulation having preservatives and humectants.

The activator may include or consist of any suitable material composition, including, but not limited to calcium salts, calcium chloride, calcium chloride dihydrate, calcium sulfate, calcium gluconate, calcium pidolate, calcium pantothenate, zinc salts, zinc pidolate, copper salts, copper sulfate, copper pidolate, manganese salts, manganese gluconate, and combinations thereof.

The following examples are intended to further illustrate the present disclosure. They are not intended to limit the disclosure in any way. Unless otherwise indicated, all parts are by weight.

EXAMPLES

Table 1 discloses exemplary inventive formulations, each of which satisfies the standards for an aqueous gel mask composition because the aqueous gel mask compositions produced from the formulations adequately spread on skin without unacceptable lumping or clumping, have acceptable levels of dripping, and produce peels which are removable from skin in a single, uniform piece.

TABLE 1

| | | | | | (wt %). | | | |
|---|---|---|---|---|---|---|---|---|
| Formulas | PH6160 | HF120RBS | CR8133 | LFR5/60 | Glycerin | Phenoxyethanol | Chlorphenesin | QS:Water |
| 1 | 0 | 1 | 1.5 | 2.5 | 15 | 0.7 | 0.2 | 79.1 |
| 2 | 0 | 2 | 1.5 | 0 | 15 | 0.7 | 0.2 | 80.6 |
| 3 | 0 | 1.5 | 3 | 0 | 15 | 0.7 | 0.2 | 79.6 |
| 4 | 2 | 0 | 0 | 2.5 | 15 | 0.7 | 0.2 | 79.6 |
| 5 | 1.5 | 0 | 1.5 | 0 | 15 | 0.7 | 0.2 | 81.1 |
| 6 | 1.5 | 0 | 1.5 | 1.25 | 15 | 0.7 | 0.2 | 79.85 |
| 7 | 1 | 0 | 3 | 0 | 15 | 0.7 | 0.2 | 80.1 |
| 8 | 1.5 | 0 | 0.75 | 0 | 15 | 0.7 | 0.2 | 81.85 |
| 9 | 1.5 | 0 | 0 | 1.25 | 15 | 0.7 | 0.2 | 81.35 |
| 10 | 1 | 0 | 2.25 | 1.25 | 15 | 0.7 | 0.2 | 79.6 |
| 11 | 2 | 0.5 | 0 | 2.5 | 15 | 0.7 | 0.2 | 79.1 |

TABLE 1-continued (wt %).

| Formulas | PH6160 | HF120RBS | CR8133 | LFR5/60 | Glycerin | Phenoxyethanol | Chlorphenesin | QS:Water |
|---|---|---|---|---|---|---|---|---|
| 12 | 1 | 1 | 0 | 1.25 | 15 | 0.7 | 0.2 | 80.85 |
| 13 | 1 | 1.5 | 0 | 2.5 | 15 | 0.7 | 0.2 | 79.1 |
| 14 | 1.5 | 1.5 | 0 | 0 | 15 | 0.7 | 0.2 | 81.1 |
| 15 | 2 | 0.5 | 0 | 1.25 | 15 | 0.7 | 0.2 | 80.35 |
| 16 | 2 | 0 | 2.25 | 0 | 15 | 0.7 | 0.2 | 79.85 |
| 17 | 1 | 2 | 0.75 | 0 | 15 | 0.7 | 0.2 | 80.35 |
| 18 | 1 | 1 | 3 | 0 | 15 | 0.7 | 0.2 | 79.1 |
| 19 | 1 | 1.5 | 1.5 | 0 | 15 | 0.7 | 0.2 | 80.1 |
| 20 | 1.5 | 0.5 | 0.75 | 0 | 15 | 0.7 | 0.2 | 81.35 |
| 21 | 0.5 | 1 | 3 | 0 | 15 | 0.7 | 0.2 | 79.6 |
| 22 | 1.5 | 0.0 | 0.9 | 0.5 | 15 | 0.7 | 0.2 | 81.2 |
| 23 | 1.2 | 0.3 | 1.2 | 0.0 | 15 | 0.7 | 0.2 | 81.4 |
| 24 | 1.7 | 0.0 | 0.8 | 0.5 | 15 | 0.7 | 0.2 | 81.1 |
| 25 | 1.4 | 0.3 | 1.5 | 0.0 | 15 | 0.7 | 0.2 | 80.9 |
| 26 | 0.3 | 0.7 | 2.8 | 0.0 | 15 | 0.7 | 0.2 | 80.3 |
| 27 | 1.2 | 0.1 | 1.0 | 0.0 | 15 | 0.7 | 0.2 | 81.7 |
| 28 | 0.3 | 1.8 | 1.8 | 0.0 | 15 | 0.7 | 0.2 | 80.2 |
| 29 | 1.1 | 1.1 | 0.0 | 1.1 | 15 | 0.7 | 0.2 | 80.8 |
| 30 | 1.4 | 0.0 | 2.0 | 0.0 | 15 | 0.7 | 0.2 | 80.7 |
| 31 | 1.3 | 0.1 | 0.8 | 0.0 | 15 | 0.7 | 0.2 | 81.9 |
| 32 | 1.6 | 0.1 | 1.0 | 0.0 | 15 | 0.7 | 0.2 | 81.4 |
| 33 | 1.2 | 1.0 | 0.0 | 2.3 | 15 | 0.7 | 0.2 | 79.6 |
| 34 | 0.4 | 1.9 | 1.1 | 0.0 | 15 | 0.7 | 0.2 | 80.7 |
| 35 | 1.1 | 0.2 | 0.9 | 0.0 | 15 | 0.7 | 0.2 | 81.9 |
| 36 | 1.5 | 0.0 | 0.5 | 0.8 | 15 | 0.7 | 0.2 | 81.3 |
| 37 | 1.5 | 0.0 | 0.9 | 0.5 | 15 | 0.7 | 0.2 | 81.2 |

Table 2 discloses non-inventive formulations, each of which fails to satisfy the standards for an aqueous gel mask composition because the aqueous gel mask compositions produced from the non-inventive formulations fail to adequately spread on skin without unacceptable lumping or clumping, have unacceptable levels of dripping leading to excessive pooling, produce peels which are not removable from skin in a single, uniform piece, or combinations thereof.

TABLE 2

(wt %).

| Formulas | PH6160 | HF120RBS | CR8133 | LFR5/60 | Glycerin | Phenoxyethanol | Chlorphenesin | QS:Water |
|---|---|---|---|---|---|---|---|---|
| N1 | 0 | 0.5 | 0 | 2.5 | 15 | 0.7 | 0.2 | 81.1 |
| N2 | 0 | 1 | 0.75 | 2.5 | 15 | 0.7 | 0.2 | 79.85 |
| N3 | 0 | 0 | 0.75 | 2.5 | 15 | 0.7 | 0.2 | 80.85 |
| N4 | 0 | 0.5 | 1.5 | 1.25 | 15 | 0.7 | 0.2 | 80.85 |
| N5 | 0 | 0.5 | 2.25 | 1.25 | 15 | 0.7 | 0.2 | 80.1 |
| N6 | 0 | 0 | 0 | 3.75 | 15 | 0.7 | 0.2 | 80.35 |
| N7 | 0 | 1.5 | 0.75 | 1.25 | 15 | 0.7 | 0.2 | 80.6 |
| N8 | 0 | 0 | 0 | 5 | 15 | 0.7 | 0.2 | 79.1 |
| N9 | 0 | 2 | 0.75 | 1.25 | 15 | 0.7 | 0.2 | 80.1 |
| N10 | 0 | 0.5 | 3 | 0 | 15 | 0.7 | 0.2 | 80.6 |
| N11 | 0.5 | 0 | 1.5 | 0 | 15 | 0.7 | 0.2 | 82.1 |
| N12 | 0.5 | 0 | 0 | 3.75 | 15 | 0.7 | 0.2 | 79.85 |
| N13 | 0.5 | 0 | 2.25 | 1.25 | 15 | 0.7 | 0.2 | 80.1 |
| N14 | 2 | 0 | 3 | 0 | 15 | 0.7 | 0.2 | 79.1 |
| N15 | 0.5 | 0 | 1.5 | 1.25 | 15 | 0.7 | 0.2 | 80.85 |
| N16 | 1.5 | 0 | 0 | 2.5 | 15 | 0.7 | 0.2 | 80.1 |
| N17 | 1 | 1 | 0 | 2.5 | 15 | 0.7 | 0.2 | 79.6 |
| N18 | 1.5 | 1.5 | 0 | 1.25 | 15 | 0.7 | 0.2 | 79.85 |
| N19 | 0.5 | 0.5 | 0 | 2.5 | 15 | 0.7 | 0.2 | 80.6 |
| N20 | 1 | 2 | 0 | 0 | 15 | 0.7 | 0.2 | 81.1 |
| N21 | 0 | 0.5 | 0 | 1.25 | 15 | 0.7 | 0.2 | 82.35 |
| N22 | 0 | 2 | 0 | 1.25 | 15 | 0.7 | 0.2 | 80.85 |
| N23 | 0 | 2 | 0 | 0 | 15 | 0.7 | 0.2 | 82.1 |
| N24 | 2 | 2 | 0 | 0 | 15 | 0.7 | 0.2 | 80.1 |
| N25 | 0.5 | 0.5 | 2.25 | 0 | 15 | 0.7 | 0.2 | 80.85 |
| N26 | 0 | 2 | 3 | 0 | 15 | 0.7 | 0.2 | 79.1 |
| N27 | 0 | 0.5 | 2.25 | 0 | 15 | 0.7 | 0.2 | 81.35 |
| N28 | 1.5 | 1.5 | 1.5 | 0 | 15 | 0.7 | 0.2 | 79.6 |
| N29 | 0 | 0.5 | 3 | 0 | 15 | 0.7 | 0.2 | 80.6 |

In general, it has been found that the inventive formulations of Table 1 fall within one of the twelve compositional ranges presented in Table 3, whereas the non-inventive formulations of Table 2 fall outside of the twelve compositional ranges presented in Table 3.

TABLE 3

(wt %).

|   | PH6160 | HF 120 RBS | CR8133 | LFR 5/60 |
|---|---|---|---|---|
| a | 0-0.25 | 1-1.5 | 1.75-3.00 | 0 |
| b | 0-0.25 | 1-2.0 | 1-1.75 | 0-2.5 |
| c | 0.25-0.75 | 1-1.5 | 3 | 0 |
| d | 0.25-0.75 | 1.5-2.0 | 1.0-1.25 | 0 |
| e | 0.75-1.25 | 0 | 2.25-3 | 0-1.25 |
| f | 0.75-1.25 | 0.5-1.0 | 0-3 | 0-1.25 |
| g | 0.75-1.25 | >1-1.5 | 0-1.5 | 0-2.5 |
| h | 1.25-1.75 | 0 | 0-1 | 0-1.25 |
| i | 1.25-1.75 | 0-0.5 | 1 | 0 |
| j | 1.25-1.75 | 1-1.5 | 0 | 0 |
| k | 1.75-2.0 | 0 | 2-2.25 | 0 |
| l | 1.75-2.0 | 0.5 | 0 | 1.25-2.5 |

Table 4 discloses exemplary inventive formulations including additives beyond those present in the exemplary inventive formulations of Table 1, each of which satisfies the standards for an aqueous gel mask composition because the aqueous gel mask compositions produced from the formulations adequately spread on skin without unacceptable lumping or clumping, have acceptable levels of dripping, and produce peels which are removable from skin in a single, uniform piece.

TABLE 4

(wt %).

| Ingredient | Example 38 | Example 39 | Example 40 | Example 41 |
|---|---|---|---|---|
| Sodium Citrate | 0.04 | 0.04 | 0.04 | 0.04 |
| Citric Acid | 0.06 | 0.04 | 0.04 | 0.04 |
| Pigments | — | 0.058 | 0.07 | 0.07 |
| Fillers | — | — | 0.05 | 1.00 |
| Pectin | — | — | 0.48 | 0.48 |
| Protonal PH6160 | 0.41 | 0.41 | 0.6 | 0.6 |
| Protonal HF120RBS | 1.86 | 1.86 | 0.41 | 0.41 |
| Protoal CR8133 | 1.11 | 1.11 | 1.86 | 1.86 |
| Antimicrobials | 0.97 | 0.97 | 0.97 | 0.97 |
| Humectants | 15 | 15 | 15 | 15 |
| Propanediol | 3 | 3 | 3 | 3 |
| Water | 77.55 | 77.49 | 76.83 | 75.88 |

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on.

All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated. As used herein, "about", unless otherwise indicated, encompasses the expected variation in quantification inherent in the typical measurement system applied thereto as well as ordinary experimental variance, as would be understood and expected by a person having ordinary skill in the art.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An aqueous gel mask composition, comprising:
   a plurality of sodium alginates constituting, by weight, between 2.2% to 4.5% of the aqueous gel mask composition; and
   water,
   wherein:
   (a) a first sodium alginate of the plurality of sodium alginates includes a molecular weight greater than a second sodium alginate of the plurality of sodium alginates;
   (b) less than 3%, by weight, of the aqueous gel mask composition includes sodium alginates having a molecular weight of at least 300 kDa;
   (c) the plurality of sodium alginates includes:
   (i) an average ratio of β-D-mannuronate to α-L-guluronate (M/G ratio) between 70:30 to 50:50;
   (ii) an average molecular weight between 150 kDa to 425 kDa;
   (iii) at least 20%, by weight, of the sodium alginates having a molecular weight of at least 250 kDa; and
   (iv) a weight ratio of sodium alginates having a molecular weight of 75 kDa or less to sodium alginates having a molecular weight of at least 250 kDa of less than 3:2; and
   (d) if the plurality of sodium alginates includes two sodium alginates each having a molecular weight of at least 250 kDa, and the two sodium alginates constitute, by weight, less than 1.25% of the aqueous gel mask composition, then the two sodium alginates include an average molecular weight of less than 375 kDa, and
   wherein the aqueous gel mask composition is reactive with an activator to form a continuous film, the activator including a salt comprising a divalent cation.

2. The aqueous gel mask composition of claim 1, wherein the salt is selected from the group consisting of calcium salts, calcium chloride, calcium chloride dihydrate, calcium sulfate, calcium gluconate, calcium pidolate, calcium pantothenate, zinc salts, zinc pidolate, copper salts, copper sulfate, copper pidolate, manganese salts, manganese gluconate, and combinations thereof.

3. The aqueous gel mask composition of claim 2, wherein the activator includes calcium chloride dihydrate.

4. The aqueous gel mask composition of claim 1, further including glycerin.

5. The aqueous gel mask composition of claim 4, wherein the glycerin constitutes, by weight, between about 10% to about 20% of the aqueous gel mask composition.

6. The aqueous gel mask composition of claim 1, further including propanediol.

7. The aqueous gel mask composition of claim 6, wherein the propanediol constitutes, by weight, between about 2% to about 4% of the aqueous gel mask composition.

8. The aqueous gel mask composition of claim 1, wherein the aqueous gel mask composition is free of fibroin.

9. The aqueous gel mask composition of claim 1, wherein the aqueous gel mask composition is free of rheology modifiers.

10. The aqueous gel mask composition of claim 1, wherein the aqueous gel mask composition is free of thickeners.

11. The aqueous gel mask composition of claim 1, wherein the first sodium alginate includes a molecular weight between about 375 kDa and about 425 kDa, and a M/G ratio of between about 65:35 to about 70:30.

12. The aqueous gel mask composition of claim 1, wherein the first sodium alginate includes a molecular weight between about 300 kDa and about 400 kDa, and a M/G ratio of between about 45:55 to about 55:45.

13. The aqueous gel mask composition of claim 1, wherein the second sodium alginate includes a molecular weight between about 300 kDa and about 400 kDa, and a M/G ratio of between about 45:55 to about 55:45.

14. The aqueous gel mask composition of claim 1, wherein the second sodium alginate includes a molecular weight between about 90 kDa and about 180 kDa, and a M/G ratio of between about 60:40 to about 70:30.

15. The aqueous gel mask composition of claim 1, wherein the second sodium alginate includes a molecular weight between about 20 kDa and about 60 kDa, and a M/G ratio of between about 25:75 to about 35:65.

16. The aqueous gel mask composition of claim 1, wherein the first sodium alginate and the second sodium alginate are selected from the group consisting of sodium alginate materials characterized by:
   a molecular weight between about 375 kDa and about 425 kDa, and a M/G ratio of between about 65:35 to about 70:30;
   a molecular weight between about 90 kDa and about 180 kDa, and a M/G ratio of between about 60:40 to about 70:30;
   a molecular weight between about 300 kDa and about 400 kDa, and a M/G ratio of between about 45:55 to about 55:45; and
   a molecular weight between about 20 kDa and about 60 kDa, and a M/G ratio of between about 25:75 to about 35:65.

17. The aqueous gel mask composition of claim 16, wherein the plurality of sodium alginates further includes a third sodium alginate having a molecular weight less than the second sodium alginate and being selected from the group consisting of sodium alginate materials characterized by:
   a molecular weight between about 300 kDa and about 400 kDa, and a M/G ratio of between about 45:55 to about 55:45; and
   a molecular weight between about 20 kDa and about 60 kDa, and a M/G ratio of between about 25:75 to about 35:65.

18. The aqueous gel mask composition of claim 17, wherein:
   the plurality of sodium alginates further includes a fourth sodium alginate;
   the first sodium alginate includes a molecular weight between about 375 kDa and about 425 kDa, and a M/G ratio of between about 65:35 to about 70:30;
   the second sodium alginate includes a molecular weight between about 90 kDa and about 180 kDa, and a M/G ratio of between about 60:40 to about 70:30;
   the third sodium alginate includes a molecular weight between about 300 kDa and about 400 kDa, and a M/G ratio of between about 45:55 to about 55:45; and the fourth sodium alginate includes a molecular weight between about 20 kDa and about 60 kDa, and a M/G ratio of between about 25:75 to about 35:65.

19. The aqueous gel mask composition of claim 1, wherein the water constitutes, by weight, between about 70% to about 80% of the aqueous gel mask composition.

20. The aqueous gel mask composition of claim 1, further including glycerin and propanediol, wherein:
the plurality of sodium alginates constitutes, by weight, about 3.4% of the aqueous gel mask composition;
the water constitutes, by weight, between about 74% to about 78% of the aqueous gel mask composition;
the glycerin constitutes, by weight, about 15% of the aqueous gel mask composition; and
the propanediol constitutes, by weight, about 3% of the aqueous gel mask composition.

21. An aqueous gel mask composition, comprising:
a plurality of sodium alginates constituting, by weight, between 2.2% to 4.5% of the aqueous gel mask composition; and
water,
wherein the plurality of sodium alginates is selected from the group consisting of:
a first sodium alginate having a molecular weight between about 375 kDa and about 425 kDa, and a ratio of β-D-mannuronate to α-L-guluronate (M/G ratio) of between about 65:35 to about 70:30;
a second sodium alginate having a molecular weight between about 90 kDa and about 180 kDa, and a M/G ratio of between about 60:40 to about 70:30;
a third sodium alginate having a molecular weight between about 300 kDa and about 400 kDa, and a M/G ratio of between about 45:55 to about 55:45; and
a fourth sodium alginate having a molecular weight between about 20 kDa and about 60 kDa, and a M/G ratio of between about 25:75 to about 35:65; and
combinations thereof,
wherein the plurality of sodium alginates is a formulation, by weight, selected from the group consisting of:
(a) 0-0.25% of the first sodium alginate, 1-1.5% of the second sodium alginate, and 1.75-3% of the third sodium alginate;
(b) 0-0.25% of the first sodium alginate, 1-2% of the second sodium alginate, 1-1.75% of the third sodium alginate, and 0-2.5% of the fourth sodium alginate;
(c) 0.25-0.75% of the first sodium alginate, 1-1.5% of the second sodium alginate, and 3% of the third sodium alginate;
(d) 0.25-0.75% of the first sodium alginate, 1.5-2% of the second sodium alginate, and 1-1.25% of the third sodium alginate;
(e) 0.75-1.25% of the first sodium alginate, 2.25-3% of the third sodium alginate, and 0-1.25% of the fourth sodium alginate;
(f) 0.75-1.25% of the first sodium alginate, 0.5-1% of the second sodium alginate, 0-3% of the third sodium alginate, and 0-1.25% of the fourth sodium alginate;
(g) 0.75-1.25% of the first sodium alginate, 1-1.5% of the second sodium alginate, 0-1.5% of the third sodium alginate, and 0-2.5% of the fourth sodium alginate;
(h) 1.25-1.75% of the first sodium alginate, 0-1% of the third sodium alginate, and 0-1.25% of the fourth sodium alginate;
(i) 1.25-1.75% of the first sodium alginate, 0-0.5% of the second sodium alginate, and 1% of the third sodium alginate;
(j) 1.25-1.75% of the first sodium alginate and 1-1.5% of the second sodium alginate;
(k) 1.75-2% of the first sodium alginate and 2-2.5% of the third sodium alginate; and
(l) 1.75-2% of the first sodium alginate, 0.5% of the second sodium alginate, and 1.25-2.5% of the third sodium alginate, and
wherein the aqueous gel mask composition is reactive with an activator to form a continuous film, the activator including a salt comprising a divalent cation.

22. An aqueous gel mask kit, comprising:
an aqueous gel mask composition, including:
a plurality of sodium alginates; and
water; and
an activator including a salt comprising a divalent cation, wherein:
the plurality of sodium alginates includes an average ratio of β-D-mannuronate to α-L-guluronate (M/G ratio) between 70:30 to 50:50;
the plurality of sodium alginates includes an average molecular weight between 150 kDa to 425 kDa;
at least 20% of the plurality of sodium alginates includes a molecular weight of at least 250 kDa;
a first sodium alginate of the plurality of sodium alginates includes a molecular weight greater than a second sodium alginate of the plurality of sodium alginates;
the aqueous gel mask composition is reactive with the activator to form a continuous film;
the plurality of sodium alginates constitutes, by weight, between 2.2% to 4.5% of the aqueous gel mask composition;
the plurality of sodium alginates includes a weight ratio of sodium alginates having a molecular weight of 75 kDa or less to sodium alginates having a molecular weight of at least 250 kDa of less than 3:2;
the aqueous gel mask composition includes, by weight, less than 3% of the plurality of sodium alginates having a molecular weight of at least 300 kDa; and
if the plurality of sodium alginates includes two sodium alginates each having a molecular weight of at least 250 kDa, and the two sodium alginates constitute, by weight, less than 1.25% of the aqueous gel mask composition, then the two sodium alginates include an average molecular weight of less than 375 kDa.

23. The aqueous gel mask kit of claim 22, wherein the activator is a liquid and is disposed in a spraying or misting apparatus.

* * * * *